United States Patent [19]

Hentschel, Jr. et al.

[11] 4,082,003

[45] Apr. 4, 1978

[54] PELLET SAMPLER AND METHOD OF SAMPLING PELLETS

[75] Inventors: Robert Carl Hentschel, Jr.; William McIntosh Gignilliat, both of Columbia, S.C.

[73] Assignee: Allied Chemical Corporation, Morris Township, N.J.

[21] Appl. No.: 771,710

[22] Filed: Feb. 24, 1977

[51] Int. Cl.² .............................................. G01N 1/20
[52] U.S. Cl. ..................................... 73/422 R; 73/424
[58] Field of Search ............................. 73/422 R, 424

[56] References Cited

U.S. PATENT DOCUMENTS

| 2,682,772 | 7/1954 | Peterson | 73/424 |
| 3,279,259 | 10/1966 | Haley et al. | 73/424 |

FOREIGN PATENT DOCUMENTS 255,643   1969   U.S.S.R. .................................. 73/424

Primary Examiner—S. Clement Swisher
Attorney, Agent, or Firm—Richard A. Anderson

[57] ABSTRACT

An improved pellet sampler and method of sampling pellets is disclosed. The apparatus is an opening in a conduit, such as the open end of a pipe, exposed to flowing pellets and communicating with an auger which revolves to remove a small portion of the flowing pellets as a sample. The improvement is the fixed opening having a plane at an angle between parallel and normal, preferably 45°, to the flow of pellets coinciding with the auger feed end and normal to the auger axis. The method is to revolve the auger at a measured rate to collect a uniform sample.

10 Claims, 1 Drawing Figure

U.S. Patent    April 4, 1978    4,082,003
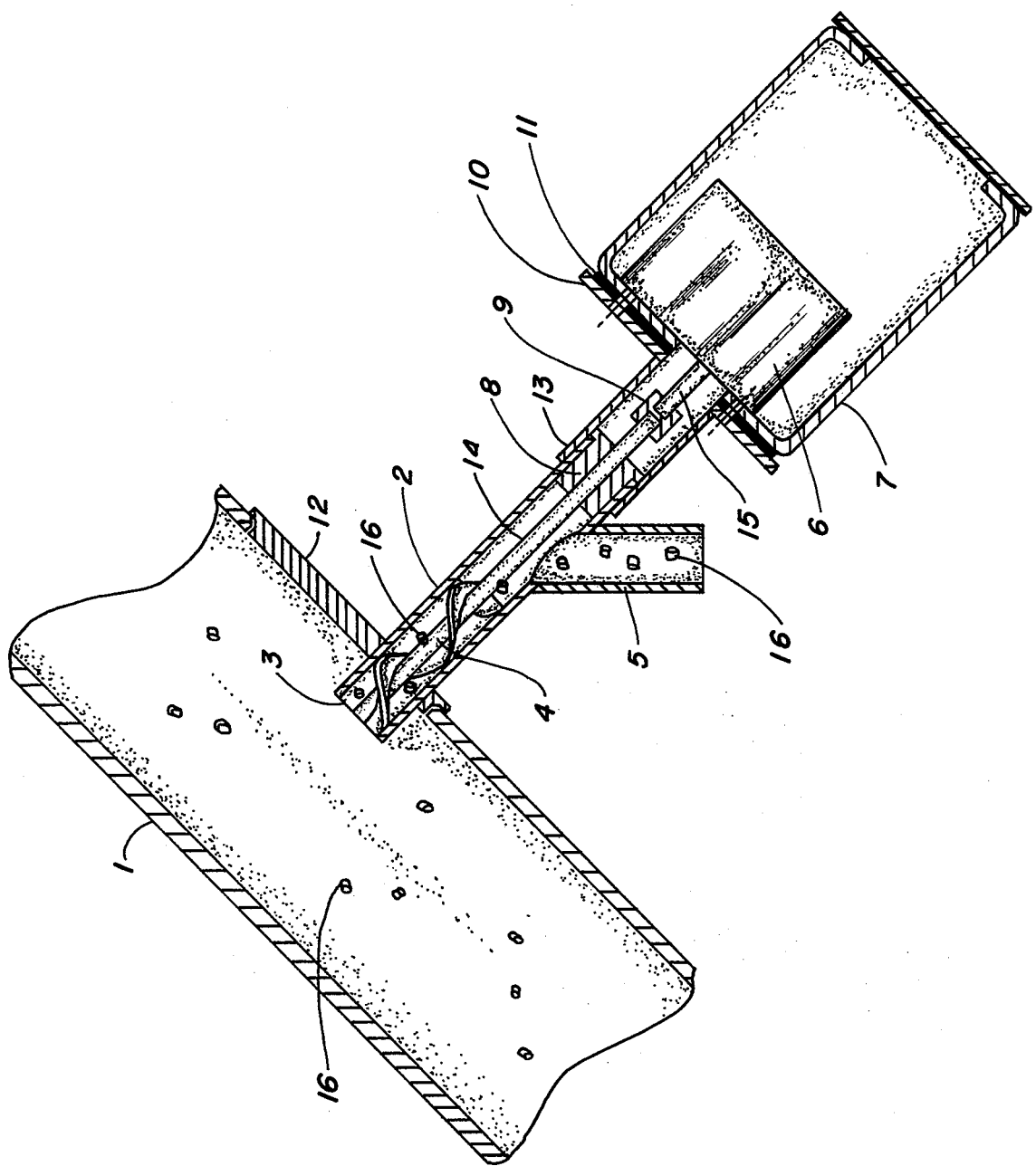

PELLET SAMPLER AND METHOD OF SAMPLING PELLETS

BACKGROUND OF THE INVENTION

This invention relates to sampling of flowing pellets with an auger to withdraw a small portion of the pellets.

Previous to auger-type samplers, and still in use today, is the familiar grab sample technique of either by hand or with an automatic mechanical device dipping into the flowing pellets with a container periodically to remove a sample. This method often produce nonrepresentative samples, and can be inaccurate even if multiple samples are averaged.

It is also known to use an auger revolving in a pipe, the pipe having an opening such as a slot exposed periodically to flowing pellets, such as in a conveyor tube, to remove a sample of pellets. For example, such an automatic sampler is shown as Model D in a Gustafson Manufacturing, Inc. Catalog No. SD-4, 6-69 VP (6600 South County Road 18, Hopkins, Minn.).

However, many of the various prior art apparatus occasionally caught a pellet in the space between the auger and the opening in the pipe or auger housing, jamming it. This can happen whenever the opening exposed to flowing pellets does not coincide with the auger feed end. Also, it is preferable to provide a sampler having minimum obstruction to flow of the flowing pellets to avoid causing an accumulation of pellets around the sampler giving nonrepresentative samples or even possible plugging.

SUMMARY OF THE INVENTION

The apparatus and method of this invention have overcome the jamming problem, provide a low obstruction to flowing pellets, and create a uniform, representative sample.

The pellet sampler is basically an auger turning in a conduit inserted in a flowing stream of pellets. The pellet flow can be either vertical or horizontal or any angle between. The sampler extracts a small portion of the chips for every revolution of the auger, giving a representative and uniform sample of an entire flow of the pellets. The amount of sample material is dependent upon the size of the auger and the speed of the motor or other driver. A timer can be installed to regulate the sampling frequency.

The apparatus is an improvement on a pellet sampling apparatus of the prior art which was an opening in a conduit exposed to flowing pellets, with the opening communicating with an auger which revolves to remove a portion of the pellets as a sample. The improvement of this invention comprises the opening being fixed and having a plane at an angle including and between parallel and normal, preferably 45°, to the flow of the pellets and normal to the axis of the drive shaft of the auger. In order to eliminate jamming of the auger, the opening must coincide with the feed end of the auger. The auger revolves at a measured rate to meter the pellets through the opening. Thus, the pellets are continuously collected at the metered rate so that a representative uniform sample is collected. Preferably, in order to have a low profile or low obstruction to the flowing chips, the opening in the conduit at the feed end of the auger is located near the periphery of the flowing pellets, such as near the circumference of a conveyor tube containing flowing pellets. The auger and tube dimensions could be altered to accomodate any size chip or pellet.

The method is an improvement on the prior art method to sample flowing pellets by removing a portion of the pellets with an auger through an opening in a conduit. The improvement comprises revolving the auger at a measured rate and continuously removing a portion of the pellets through the opening which is fixed and which coincides with the feed end of the auger. The opening also has a plane at an angle between and including parallel and normal, preferably 45°, to the flow of pellets and normal to the drive shaft of the auger. The removed portion is continuously collected in a sample so that the sample is a uniform, representative sample of the pellets not collected during the time the collected portion was removed from the flow of pellets. Preferably, the measured rate is adjusted to remove from between about 10 to about 10,000 ppm by weight of the flowing pellets. Also, preferably, the auger is continuously revolved at a preferable rate of between about 1/20 and about 25 revolutions per minute. The auger could also be periodically revolved on a time schedule, preferably an automatic time schedule.

DESCRIPTION OF THE PREFERRED EMBODIMENT

Referring to the FIGURE, a cross-sectional view of the apparatus is shown.

Pellets 16 flow through tube 1 and are sampled into pipe or conduit 2 having an open end, opening 3. Only a few pellets 16 are shown for clarity. In most instances the pellets 16 will actually be more tightly packed. Conduit 2 has screw or auger 4 extending between opening 3 and draw-off conduit 5. The drive shaft 14 for auger 4 is sealed below draw-off conduit 5 by bushing 8 and is coupled to a motor 6 hacing drive shaft 15 by coupling 9. Motor 6 is protected by sealed box 7 attached to conduit 2 by means of flange 10 and shaft housing 13 and sealed by gasket 11. Conduit 2 is fitted into an opening in tube 1 by means of a tight fitting plate 12, which can be tack welded in place.

Pellets 16 flowing through tube 1, usually by gravity, are continuously sampled through opening 3 in conduit 2 by a measured metered amount determined by the revolutions per minute of auger 4. Pellets 16 passing through conduit 2 drop from the bottom of auger 4 and pass to draw-off conduit 5 to be collected or accumulated as a sample. Seal 8 prevents pellets 16 from passing along drive shaft 14. The feed end of the auger 4 is at opening 3, which is fixed. In this embodiment, the angle of the plane of opening 3 is shown parallel to the flow of pellets.

EXAMPLE

In an actual operation, flowing polymer chips or pellets falling into a Young, paddle-type feeder are sampled just prior to the paddle of the feeder by use of this invention. The auger revolves at one revolution per minute (rpm). About 2,500 pounds per hour of polymer pellets flow through the conveyor tube with a one-half pound sample being withdrawn each hour by the apparatus of the invention.

We claim:

1. In a pellet sampling apparatus comprising an opening in a conduit exposed to flowing pellets, said opening communicating with an auger which revolves to remove a portion of said pellets as a sample, the improvement comprising said opening being fixed and having a plane at an angle including and between parallel and normal to the flow of said pellets and normal to the axis of the drive shaft of said auger, said opening coinciding with the feed end of said auger, said auger revolving at a measured rate to meter said pellets through said opening, said flowing pellets having a periphery, and said opening being located near the periphery of said flowing pellets, providing minimum obstruction to flow of flowing pellets to avoid causing an accumulation of pellets around the sampler, whereby said pellets collected at said metered rate so that a representative, uniform sample is collected.

2. The apparatus of claim 1 wherein said angle is about 45°.

3. In a method to sample flowing pellets by removing a portion of said pellets with an auger through an opening in a conduit, the improvement comprising revolving said auger at a measured rate, removing a portion of said pellets through said opening which is fixed and coincides with the feed end of said auger and which has a plane at an angle between and including parallel and normal to the flow of said pellets and normal to the drive shaft of said auger, said flowing pellets having a periphery, and said opening being located near the periphery of said flowing pellets, providing minimum obstruction to flow of flowing pellets to avoid causing an accumulation of pellets around the sampler, collecting said removed portion as a sample, so that said sample is uniform and representative of the pellets not collected during the time the collected portion was removed from the flow of pellets.

4. The method of claim 3 wherein said rate is adjusted to remove from between about 10 to about 10,000 ppm by weight of said flowing pellets.

5. The method of claim 3 wherein said auger is continuously revolved.

6. The method of claim 3 wherein said angle is about 45°.

7. The method of claim 5 wherein said rate is between about 1/20 and about 25 revolutions per minute.

8. The method of claim 3 wherein said auger is periodically revolved on a timed schedule.

9. The method of claim 8 wherein said timed schedule is automatic.

10. The method of claim 7 wherein said angle is about 45°.

* * * * *